(12) United States Patent
LeMaitre et al.

(10) Patent No.: US 9,232,961 B2
(45) Date of Patent: Jan. 12, 2016

(54) OVER-THE-WIRE VALVULOTOMES

(71) Applicant: LeMaitre Vascular, Inc., Burlington, MA (US)

(72) Inventors: George W. LeMaitre, Boston, MA (US); Ryan H. Connelly, Topsfield, MA (US); Jahi C. Gist, Chicago, IL (US); Matthew G. Maher, Boston, MA (US)

(73) Assignee: LeMaitre Vascular, Inc., Burlington, MA (US)

( * ) Notice: Subject to any disclaimer, the term of this patent is extended or adjusted under 35 U.S.C. 154(b) by 138 days.

(21) Appl. No.: 13/908,469

(22) Filed: Jun. 3, 2013

(65) Prior Publication Data
US 2013/0267974 A1 Oct. 10, 2013

Related U.S. Application Data

(63) Continuation of application No. 13/166,137, filed on Jun. 22, 2011, now Pat. No. 8,491,614.

(60) Provisional application No. 61/357,347, filed on Jun. 22, 2010.

(51) Int. Cl.
*A61B 17/32* (2006.01)
*A61B 17/3207* (2006.01)
(Continued)

(52) U.S. Cl.
CPC ... *A61B 17/320725* (2013.01); *A61B 17/32075* (2013.01); *A61B 2017/22097* (2013.01); *A61B 2019/481* (2013.01)

(58) Field of Classification Search
None
See application file for complete search history.

(56) References Cited

U.S. PATENT DOCUMENTS 3,837,345 A 9/1974 Matar
4,768,508 A 9/1988 Chin et al.
4,952,215 A 8/1990 Ouriel et al.
(Continued)

FOREIGN PATENT DOCUMENTS

WO WO 99/23961 5/1999
WO WO 2011/107249 9/2011
WO WO 2011/163322 12/2011

OTHER PUBLICATIONS

PCT International Search Report based on PCT/US2011/041383 dated Oct. 11, 2011.
(Continued)

*Primary Examiner* — Tuan V Nguyen
(74) *Attorney, Agent, or Firm* — Greenberg Traurig, LLP; David J. Dykeman; Roman Fayerberg

(57) ABSTRACT

Over-the-wire self-sizing, self-centering valvulotomes sufficiently designed to cut valves through a wide range of vein diameters and adjust to the internal diameter of a vein as the valvulotome is being drawn through the vessel, and methods of use thereof during certain medical procedures that involve splitting valves, are disclosed herein. In an embodiment, an over-the-wire valvulotome includes a catheter having a proximal end, a distal end, and a longitudinal axis therebetween, wherein a first portion of a plurality of cutting tools engage the catheter at the distal end, and wherein an actuation mechanism engages the catheter at the proximal end; a retainer for temporarily shielding a second portion of the plurality of cutting tools, wherein the second portion includes cutting blades; and a sheath slidably movable over the plurality of cutting blades, wherein the catheter and the retainer have internal diameters configured for passing over a guidewire.

15 Claims, 11 Drawing Sheets

(51) Int. Cl.
   *A61B 17/22* (2006.01)
   *A61B 19/00* (2006.01)

(56) References Cited

U.S. PATENT DOCUMENTS

| | | | |
|---|---|---|---|
| 5,069,679 A | 12/1991 | Taheri | |
| 5,074,871 A * | 12/1991 | Groshong | 606/170 |
| 5,133,725 A | 7/1992 | Quadri | |
| 5,152,771 A | 10/1992 | Sabbaghian et al. | |
| 5,156,610 A | 10/1992 | Roger | |
| 5,158,564 A | 10/1992 | Schnepp-Pesch et al. | |
| 5,171,316 A | 12/1992 | Mehigan | |
| 5,178,625 A | 1/1993 | Groshong | |
| 5,234,450 A | 8/1993 | Segalowitz | |
| 5,269,764 A | 12/1993 | Vetter et al. | |
| 5,282,484 A | 2/1994 | Reger | |
| 5,304,189 A | 4/1994 | Goldberg et al. | |
| 5,352,232 A | 10/1994 | Cohen | |
| 5,658,301 A | 8/1997 | Lemaitre et al. | |
| 6,090,118 A | 7/2000 | McGuckin, Jr. | |
| 6,263,248 B1 | 7/2001 | Farley et al. | |
| 6,565,588 B1 | 5/2003 | Clement et al. | |
| 6,602,264 B1 | 8/2003 | McGuckin, Jr. | |
| 6,758,851 B2 | 7/2004 | Shiber | |
| 6,818,002 B2 | 11/2004 | Shiber | |
| 7,037,316 B2 | 5/2006 | McGuckin, Jr. et al. | |
| 7,108,704 B2 | 9/2006 | Trerotola | |
| 7,507,246 B2 | 3/2009 | McGuckin et al. | |
| 7,645,261 B2 | 1/2010 | Hinchliffe | |
| 7,717,930 B2 | 5/2010 | Paul, Jr. et al. | |
| 7,744,621 B2 | 6/2010 | Paul et al. | |
| 7,909,801 B2 | 3/2011 | Hinchliffe | |
| 7,909,862 B2 | 3/2011 | Garrison et al. | |
| 8,091,202 B2 | 1/2012 | Galati et al. | |
| 8,372,097 B2 | 2/2013 | Buchbinder et al. | |
| 8,491,614 B2 | 7/2013 | LeMaitre et al. | |
| 2005/0125016 A1 | 6/2005 | Trerotola | |
| 2005/0192606 A1 | 9/2005 | Paul, Jr. et al. | |
| 2005/0209617 A1 | 9/2005 | Koven et al. | |
| 2008/0255595 A1 | 10/2008 | Buchbinder et al. | |
| 2013/0116500 A1 | 5/2013 | Kohl et al. | |

OTHER PUBLICATIONS

USPTO Office Action in U.S. Appl. No. 13/166,137 mailed Jan. 4, 2013.

Supplemental European Search Report based on EP 11 79 7292 dated Nov. 18, 2013.

* cited by examiner

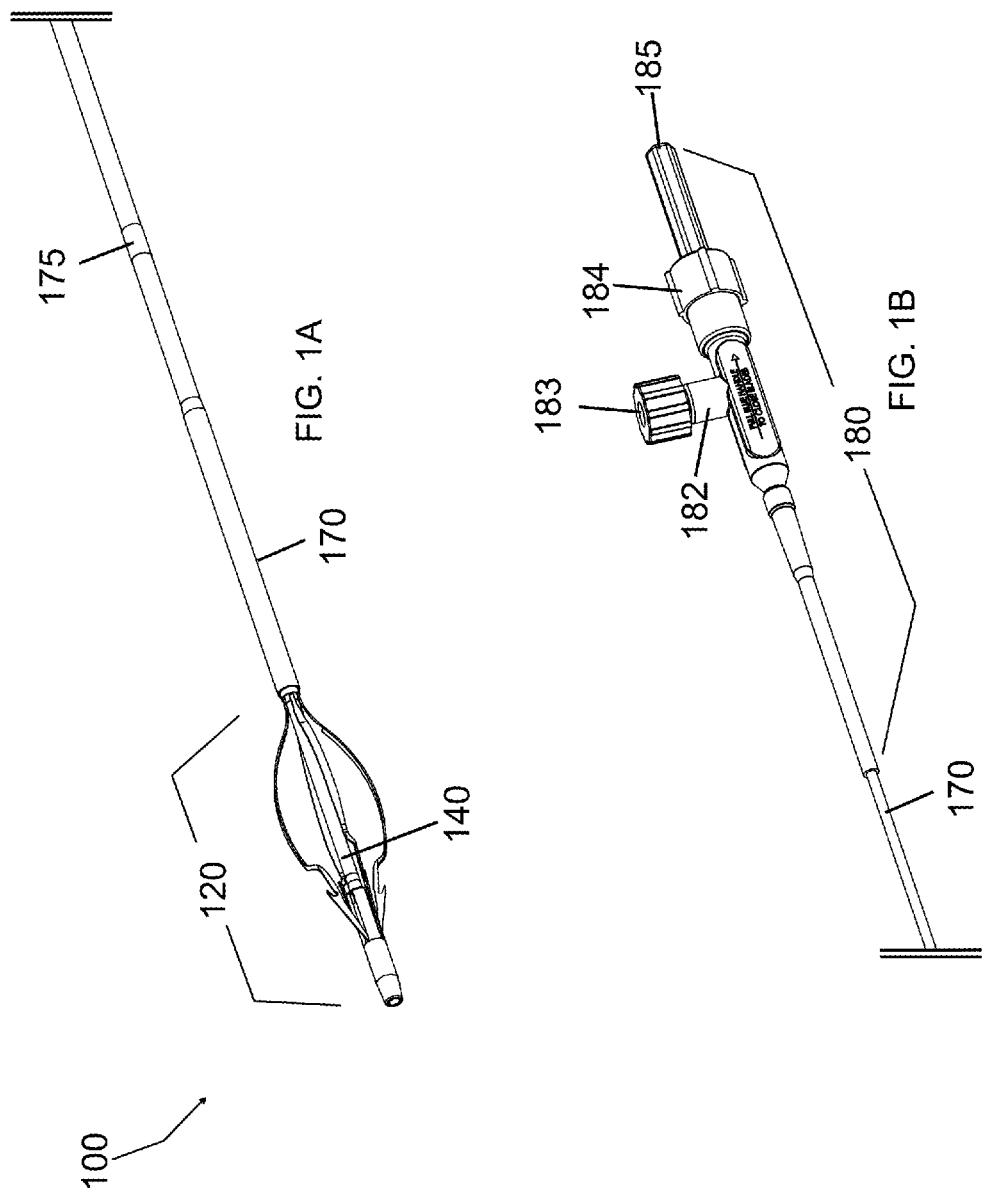

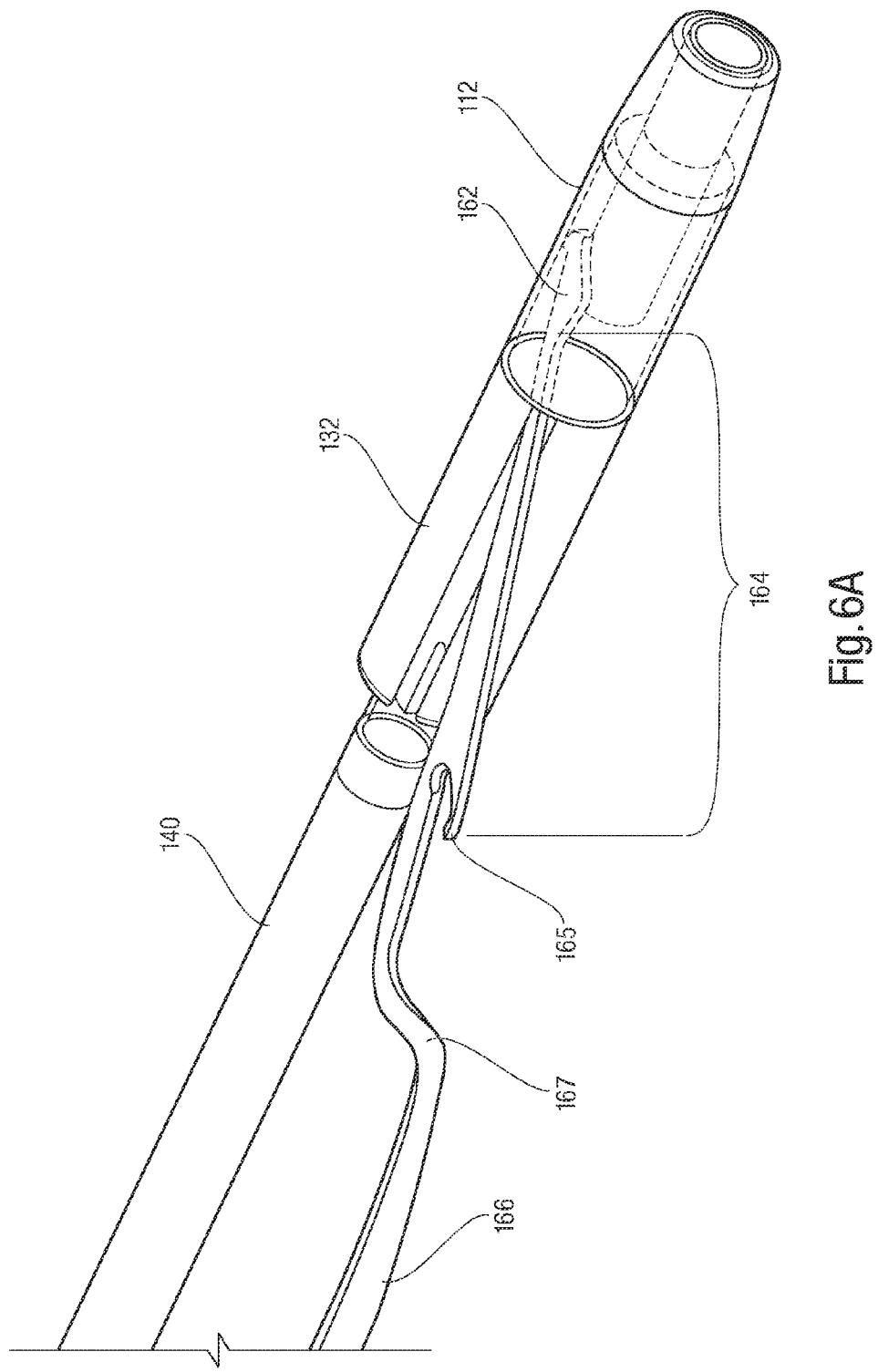

OVER-THE-WIRE VALVULOTOMES

RELATED APPLICATIONS

This application is a continuation of, and claims the benefit of and priority to, U.S. application Ser. No. 13/166,137, filed on Jun. 22, 2011, now U.S. Pat. No. 8,491,614, and U.S. Provisional Application Ser. No. 61/357,347, filed Jun. 22, 2010, the entirety of these applications are hereby incorporated herein by reference for the teachings therein.

FIELD

The presently disclosed embodiments relate to blood vessel instruments with self-centering structure and more particularly to over-the-wire valvulotomes and methods of use thereof.

BACKGROUND

Peripheral vascular disease (PVD), also known as peripheral artery disease (PAD) or peripheral artery occlusive disease (PAOD), includes all diseases caused by the obstruction of large arteries in the arms and legs; and it also includes a subset of diseases classified as microvascular diseases resulting from episodal narrowing of the arteries (raynauds), or widening thereof (erythromelalgia) i.e. vascular spasms. PVD can result from atherosclerosis, inflammatory processes leading to stenosis, an embolism, or thrombus formation. PVD causes either acute or chronic ischemia (lack of blood supply), typically of the legs.

Some patients suffering from PVD present to their surgeon with insufficient blood flow in their lower extremities. This disease manifests itself along a spectrum: from discomfort after walking to gangrenous toes and/or feet. Surgical bypass using the saphenous vein is the gold standard of treatment for severe PVD. The in situ method of surgical bypass involves leaving the saphenous vein in its native bed and cutting the one-way check valves (a procedure known as a valvulotomy) which would normally insure venous blood flow towards the heart. Without these valves the surgeon is able to utilize the vein as an arterial conduit, in effect "arterializing" the vein. Valvulotomies are typically performed using valvulotomes.

SUMMARY

According to aspects illustrated herein, there is disclosed over-the-wire ("OTW") self-centering and self-sizing valvulotomes. In an embodiment, an OTW valvulotome of the present disclosure has self-sizing, self-centering cutting devices with self-centering capabilities for use within a tubular passageway.

According to aspects illustrated herein, there is disclosed an OTW self-sizing, self-centering valvulotome that includes a catheter having a proximal end, a distal end, and a longitudinal axis therebetween, wherein a first portion of a plurality of cutting tools engage the catheter at the distal end, and wherein an actuation mechanism engages the catheter at the proximal end; a retainer for temporarily shielding a second portion of the plurality of cutting tools, wherein the second portion includes cutting blades; and a sheath slidably movable over the plurality of cutting blades, wherein the catheter and the retainer have internal diameters configured for passing over a guidewire.

According to aspects illustrated herein, there is disclosed an OTW self-sizing, self-centering valvulotome that includes a protective sheath having a lumen; a catheter having a catheter lumen, a distal portion, and a proximal portion, the catheter being partly and slidably disposed within the protective sheath; a retainer having a retainer lumen and at least four slots, the retainer fixedly engaging the distal portion of the catheter so as to provide a continuous internal channel for a guidewire; a self-sizing, self-centering cutting unit having at least four cutting tools, wherein each cutting tool comprises: a first end fixedly engaged to the distal portion of the catheter; a second end movably positioned within and guided by the slot of the retainer, the second end having a cutting blade with a recessed cutting edge; a self-sizing, self-centering resilient arm connecting the first end with the second end; and a radially bent shaped neck transitioning between the arm and the second end, the neck sufficiently designed to accommodate an outer circumference of the catheter; and a dual-purpose control mechanism attached to the protective sheath's proximal end and allowing the passage therethrough of the catheter, such that a user of the valvulotome can sheathe and unsheathe the cutting tools by sliding the catheter distally or proximally relative to the protective sheath, or slide the sheath distally or proximally relative to the catheter.

According to aspects illustrated herein, there is disclosed a method of preparing a vein for a valvulotomy procedure using an OTW self-sizing, self-centering valvulotome of the present disclosure.

According to aspects illustrated herein, there is disclosed a method of preparing a vein for in situ arterial bypass surgery using an OTW self-sizing, self-centering valvulotome of the present disclosure.

According to aspects illustrated herein, there is disclosed a method of performing a valvulotomy procedure that includes inserting an over-the-wire self-sizing, self-centering valvulotome over a guidewire and into the vein at a distal access point, wherein the valvulotome comprises: a catheter having a proximal end, a distal end, and a longitudinal axis therebetween, wherein a first portion of a plurality of cutting tools engage the catheter at the distal end, and wherein an actuation mechanism engages the catheter at the proximal end; a retainer for temporarily shielding a second portion of the plurality of cutting tools, wherein the second portion includes cutting blades; and a sheath slidably movable over the plurality of cutting blades; feeding the valvulotome into the vein with the cutting unit sheathed, until the cutting unit is past a most proximal valve in the vein; manipulating the actuation mechanism to unsheath the cutting unit to release the cutting blades; and withdrawing the valvulotome from the vein, thereby severing each valve in the vein.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIGS. 1A and 1B show perspective cutaway views of an embodiment of an over-the-wire (OTW) valvulotome of the present disclosure in the normal position. FIG. 1A shows the distal portion of the OTW valvulotome. FIG. 1B shows the proximal portion of the OTW valvulotome;

FIG. 2A shows the distal portion of the OTW valvulotome. FIG. 2B shows the proximal portion of the OTW valvulotome;

FIGS. 6A and 6B show perspective views of the distal portion of the OTW valvulotome of FIG. 1A in the normal and abandon positions of use, respectively;

Figure 2A:
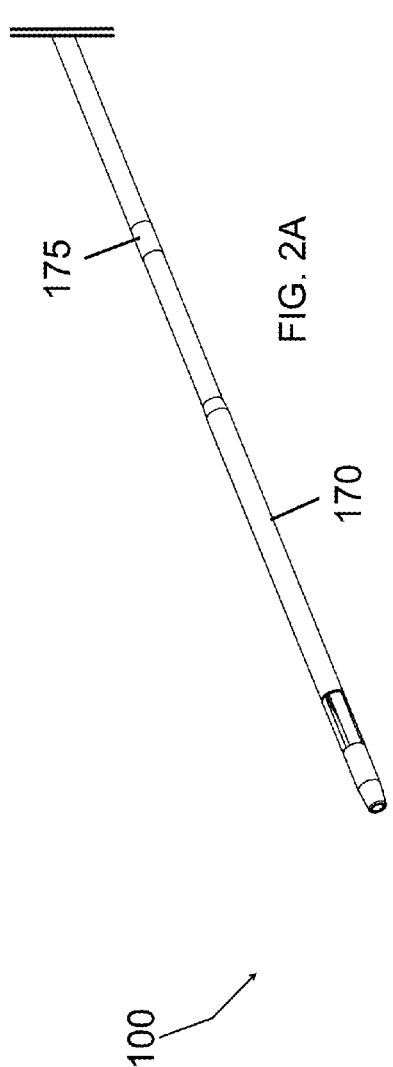
FIGS. 2A and 2B show perspective views of the OTW valvulotome of FIGS. 1A and 1B in the abandoned position.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The embodiments disclosed herein relate to over-the-wire ("OTW") self-sizing, self-centering valvulotomes and methods of use thereof during certain medical procedures that involve splitting valves. In an embodiment, an OTW valvulotome of the present disclosure is used during in situ arterial bypass surgery. In an embodiment, an OTW valvulotome of the present disclosure is used during a periphery arterial bypass surgery. In an embodiment, an OTW valvulotome of the present disclosure is used during a coronary arterial bypass surgery. In an embodiment, an OTW valvulotome of the present disclosure is used during an arteriovenous fistula (AV fistula) procedure, for example to allow access to the vascular system for hemodialysis.

In an embodiment, an OTW valvulotome of the present disclosure is used for performing minimally-invasive valvulotomy. In an embodiment, an OTW valvulotome of the present disclosure is sufficiently sized and shaped to be used in a valvulotomy procedure. In an embodiment, an OTW valvulotome of the present disclosure is sufficiently sized and shaped to be used in an in situ arterial bypass surgery down the entire leg of a patient. In an embodiment, an OTW valvulotome of the present disclosure is sufficiently sized and shaped to be used in an in situ arterial bypass surgery down a portion of the leg of a patient, for example, in a surgery where the surgeon has to harvest only above or below the knee. In an embodiment, an OTW valvulotome of the present disclosure can effectively, efficiently, and automatically disable valves, yet not damage the vein wall. In an embodiment, an OTW valvulotome of the present disclosure can cut valves through a wide range of vein diameters, thus one size cutting unit allows for effective valve disruption through a wide range of vein diameters. In an embodiment, an OTW valvulotome of the present disclosure can be moved freely up or down the vein during the valve disruption process, allowing multiple passes at each valve site without removing the valvulotome.

In an embodiment, an OTW valvulotome of the present disclosure is a sterile, biocompatible, hemostatic, disposable device that lyses venous valves for distal bypass and other procedures. In an embodiment, an OTW valvulotome of the present disclosure is sufficiently designed for single use and is disposable.

In an embodiment, an OTW valvulotome of the present disclosure is sufficiently designed to include centering hoops that keep the valvulotome centered in a vein and prevent the valve-cutting blades from damaging the vein wall. In an embodiment, the size of the centering hoops and blades adjusts to the internal diameter of a vein as the valvulotome is being drawn through the vessel. In an embodiment, an OTW valvulotome of the present disclosure is sufficiently designed to allow a plurality of cutting blades to automatically bias against a vein wall. In an embodiment, an OTW valvulotome of the present disclosure includes a safety feature whereby the cutting blades can be retracted or sheathed to protect a vein wall if the need arises. In an embodiment, an OTW valvulotome of the present disclosure is used with a guidewire to assist in the insertion, navigation and positioning of the valvulotome in a vein. In an embodiment, use of a guidewire in conjunction with an OTW valvulotome of the present disclosure results in increased safety for initial passage of the valvulotome through a vein. In an embodiment, use of a guidewire in conjunction with an OTW valvulotome of the present disclosure results in the ability to confirm valvulotome location via an imaging technique. In an embodiment, use of a guidewire in conjunction with an OTW valvulotome of the present disclosure results in increase speed and safety when passing the valvulotome multiple times over a guidewire through a vein.

In an embodiment, an OTW valvulotome of the present disclosure has some inherent radiopacity due to some of the components of the OTW valvulotome being fabricated from metal materials and the associated guidewire which can be radiopaque. In an embodiment, an OTW valvulotome of the present disclosure is sufficiently designed to allow for fluid insertion or removal at or near the cutting unit. In an embodiment, an OTW valvulotome of the present disclosure is sufficiently designed to allow for fluid pressure monitoring at the site of fluid insertion or removal by a surgeon during the procedure. An OTW valvulotome of the present disclosure may likewise be used in other, non-surgical applications that require a self-centering device. The inner channel of an OTW valvulotome of the present disclosure can be used for the insertion of other endovascular instruments into the vein for surgical bypass or diagnosis (e.g. tributary ligation, anastomosis, biopsy, endoscopy, etc.).

FIGS. 1A, 1B, 2A, and 2B show perspective views of an embodiment of an OTW valvulotome 100 of the present disclosure in normal (FIGS. 1A-1B) and abandon (FIGS. 2A-2B) positions of use. The OTW valvulotome 100 includes a catheter 140 having a distal portion (FIGS. 1A and 2A) with a self-sizing, self-centering cutting unit 120, a proximal portion (FIGS. 1B and 2B) terminating in a control mechanism 180, and a longitudinal axis therebetween. The catheter 140 is partly and slidably disposed within a protective sheath 170. In an embodiment, the sheath 170 is removable. In an embodiment, the sheath 170 is a thin plastic tubular member which is a loose sliding fit on the outer diameter of the catheter 140. In an embodiment, the sheath 170 is manufactured from a polytetrafluoroethylene material. In an embodiment, the sheath 170 is manufactured from a thermoplastic material. In an embodiment, the sheath 170 covers the cutting unit 120 during insertion (FIG. 2A), allowing for smooth advancement to the proximal anastomosis. In an embodiment, the sheath 170 includes at least one safety marking 175 which can help alert a user when the cutting portion of a cutting blade is nearing the exit point of the vessel. As illustrated in FIG. 2A, the cutting unit 120 is in a sheathed position, completely encased by the sheath 170. When the sheath 170 is slid, a plurality of radially mounted, retractable cutting blades of the cutting unit 120 are in an open "normal" position, as illustrated in FIG. 1A.

Figure 2B:
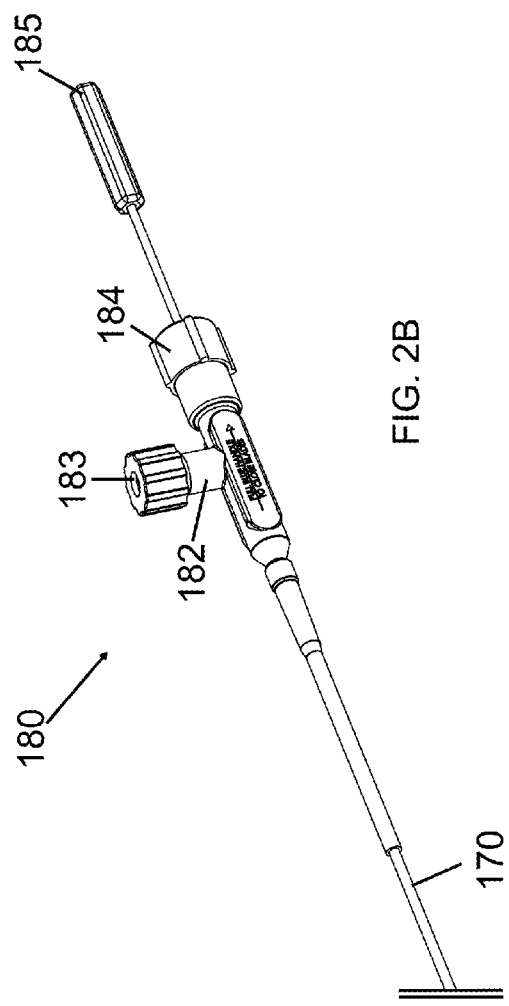

As illustrated in FIGS. 1B and 2B, in an embodiment, the control mechanism 180 is a dual-purpose control mechanism attached to the sheath 170. In an embodiment, the control mechanism 180 is sufficiently designed to serve as a handle for a user. The control mechanism 180 may comprise a T-valve segment 182, having an access port 183 and a terminal end 184, disposed partly within the proximal end of the sheath 170, the terminal end of the T-valve segment 182 being adapted to allow engagement of a pull handle 185 affixed to the proximal end of the catheter 140. In an embodiment, a tube stiffener is positioned over the catheter 140 proximal to the T-valve segment 182. In an embodiment, the control mechanism 180 is sufficiently designed to expand/contract the plurality of cutting blades of the cutting unit 120 as a user actuates the mechanism.

When the pull handle 185 engages the terminal end of the T-valve segment 182 (FIG. 1B), a fluid-tight seal is created, allowing the introduction of a diagnostic (for example, saline) or therapeutic fluid (for example, anticoagulant solutions) to the distal end of the sheath 170 via the T-valve access port 183 and the lumen of the sheath 170. The sheath 170 serves as a fluid conduit, allowing irrigation with heparinized saline and/or continuous pressure monitoring during a valvulotomy procedure. The safety stripe 175 located on the sheath 170 of the OTW valvulotome 100 can be about 3.5 cm beyond the distal end of the sheath 170. Seeing the safety stripe 175 upon withdrawal serves as a warning that the user is near the end of the OTW valvulotome 100, and that the cutting unit 120 should be closed to stow the cutting blades for final withdrawal from the vein. The T-valve access port 183 accepts a syringe, which can be attached to a syringe holding, for example, heparinized saline. Those skilled in the art will recognize that segment 182 can be any size or shape (for example, a Y-valve with multiple access ports) and still be within the scope and spirit of the present disclosure. Those skilled in the art will recognize that pull handle 185 can be any size and shape as long as the handle is configured to actuate and deploy the cutting blades of the cutting unit.

Figure 3:
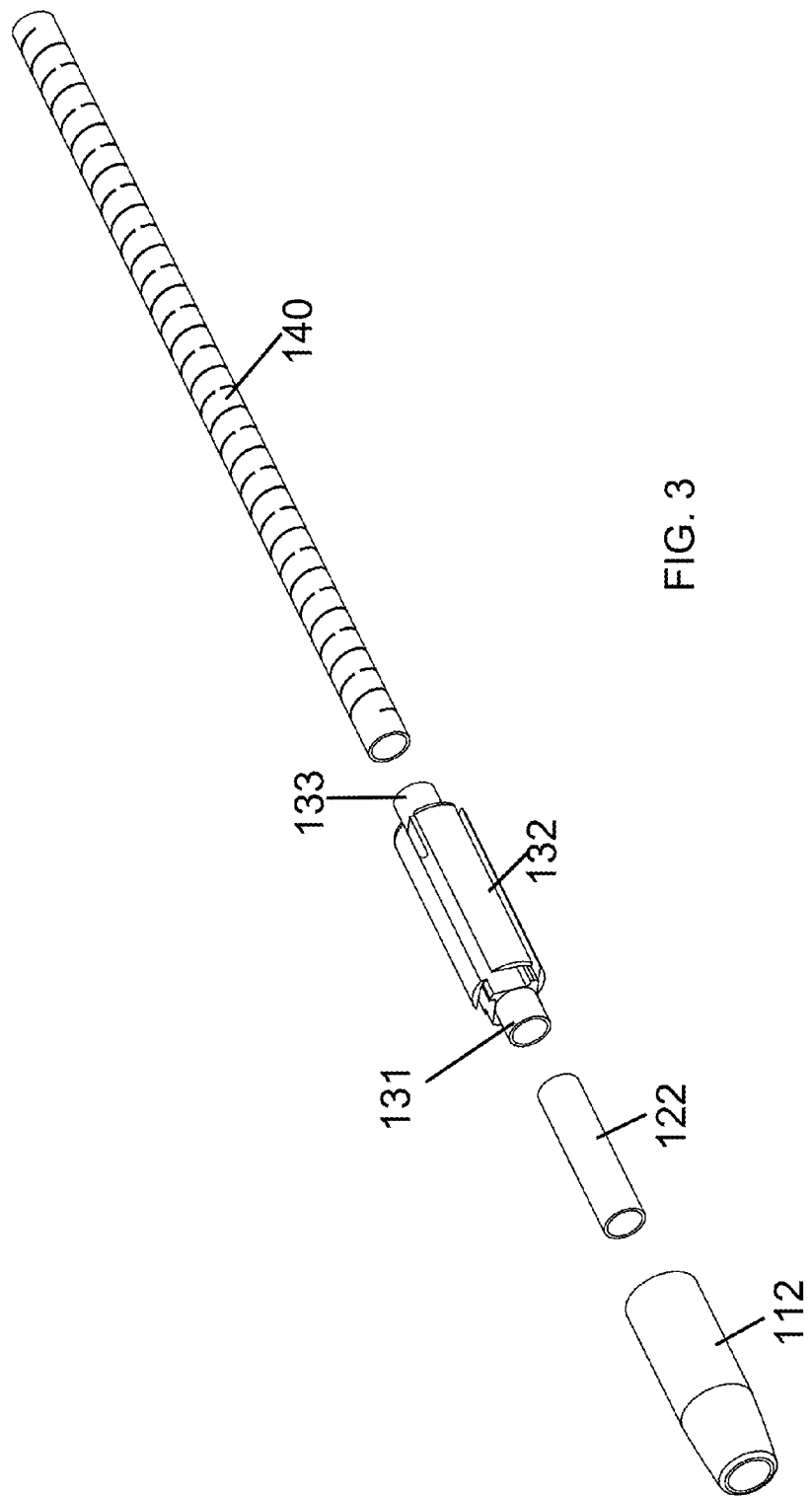
FIG. 3 shows a perspective exploded view of an embodiment of some of the components of a distal portion of the OTW valvulotome of FIG. 1A.

FIG. 3 shows a perspective exploded view of an embodiment of some of the components of a distal portion of the OTW valvulotome 100 of FIG. 1A. As illustrated in FIG. 3, the distal end of the catheter 140 engages a proximal end profile 133 of a retainer 132. A distal end profile 131 of the retainer 132 engages a proximal end of a hypotube 122, and a distal end of the hypotube 122 can be partially or completely disposed within an atraumatic tip 112. In an embodiment, the atraumatic tip 112 is fabricated from one part. In an embodiment, the atraumatic tip 112 is fabricated from more than one part, for example, a cap and a tip. In an embodiment, the atraumatic tip 112 is a machined plastic part. In an embodiment, the atraumatic tip 112 is a machined metal part. In an embodiment, the hypotube 122 is press-fitted into the atraumatic tip 112. The distal end of the OTW valvulotome 100 of the present disclosure is sufficiently designed to be atraumatically introduced into a vessel.

In an embodiment, the atraumatic tip 112, the catheter 140, the retainer 132, and the hypotube 122 are separate pieces that can be seam-welded, face-welded, butt-welded, spot-welded, soldered, adhesive bonded, chemically bonded or mechanically fastened together. The catheter 140, the retainer 132, and the hypotube 122, when engaged, form a continuous internal channel, allowing the OTW valvulotome 100 to be advanced over a guidewire. In an embodiment, the internal channel amounts to half the cross-sectional area of the distal portion of the OTW valvulotome 100, without a substantial change to the outer diameter. The guidewire would run coaxially through the catheter 140, the retainer 132, the hypotube 122 and the atraumatic tip 112.

In an embodiment, the catheter 140 is a multilayered tube, manufactured by extruding a tube, braiding or coiling over the tube with wire or polymer, and extruding an outer jacket over the braid or coil. The tube might then be drawn through a hot die to fuse the different layers together. In an embodiment, the catheter 140 includes at least a portion that is flexible. In an embodiment, the entire catheter 140 is flexible. In an embodiment, the catheter 140 includes at least a portion that is rigid. In an embodiment, the catheter 140 includes at least a portion having laser-cut side slots (FIG. 3). In an embodiment, the catheter 140 is a straight extension. In an embodiment, the catheter 140 is a curved extension. In an embodiment, the catheter 140 is manufactured from a metal material. In an embodiment, the catheter 140 is manufactured from a nitinol material. In an embodiment, the catheter 140 is manufactured from a stainless steel material. In an embodiment, the stainless steel material has multiple small sections of the wall cut away to increase the flexibility of the catheter 140. In an embodiment, the catheter 140 is a naked braid In an embodiment, the catheter 140 is non-braided or non-coiled. In an embodiment, the catheter 140 is manufactured from a thin material configured to maintain strength and pushability by extruding a braid or coil with a plastic coating/extrusion over the top.

Figure 4:
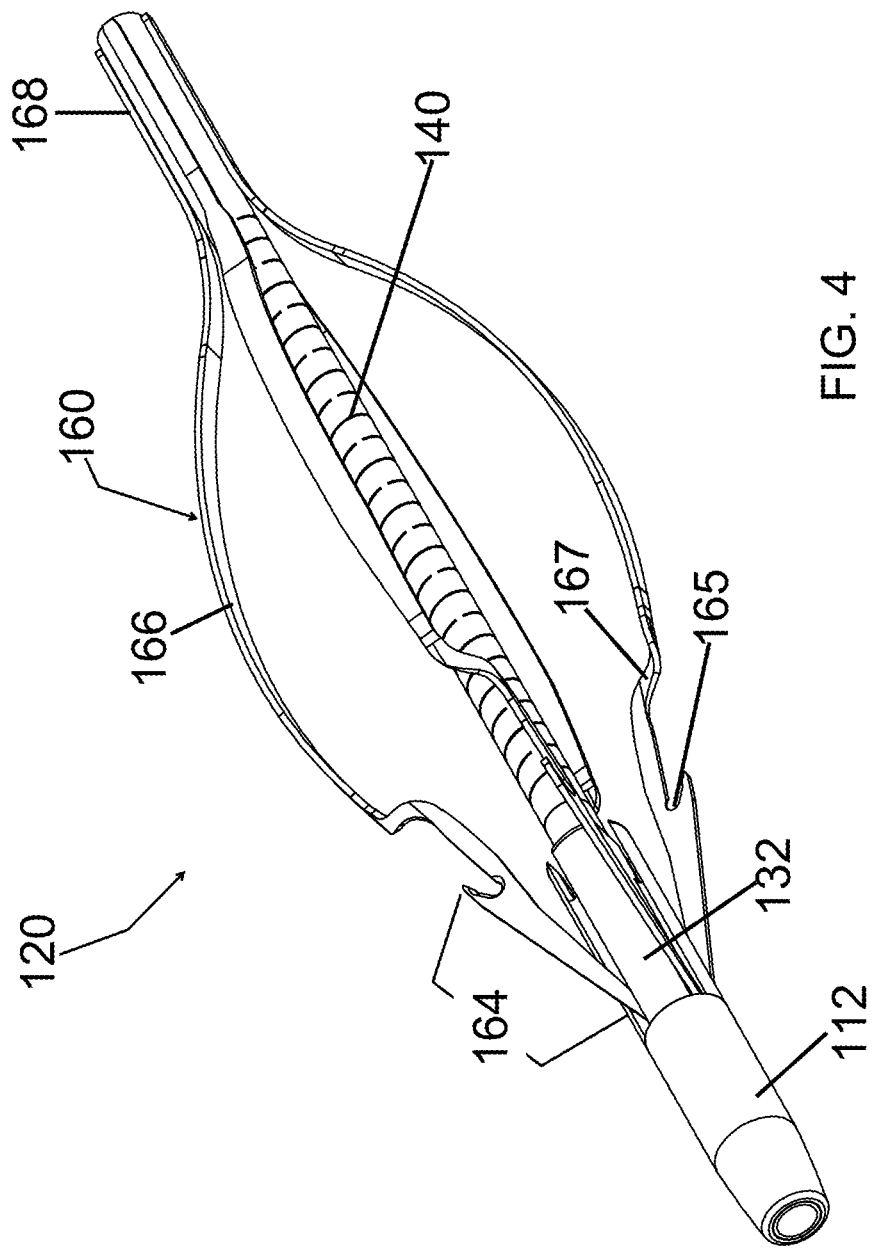
FIG. 4 shows a perspective view of an embodiment of a cutting unit of the OTW valvulotome of FIG. 1A in the normal position.

FIG. 4 shows a perspective view of an embodiment of a cutting unit 120 of the OTW valvulotome 100 of FIG. 1A in the normal position. Cutting unit 120 generally includes four self-centering, self-sizing cutting tools 160 each having a first, attached end 168 equally radially mounted on the distal portion of the catheter 140, a second, unattached end 162 (visible in FIGS. 6A and 6B) with a cutting blade 164 having a recessed cutting edge 165, and a self-sizing, self-centering arm/hoop 166. The first ends 168 of each of the cutting tools 160 fixedly engage a distal portion of the catheter 140. The cutting blades 164 of each of the cutting tools 160 are temporarily shielded by the retainer 132 during entry and removal of the valvulotome 100. Each cutting blade 164 has an upper, non-cutting outermost edge shielding the cutting edge 165 disposed inwardly therefrom relative to the catheter 140 such that the cutting edge 165 is oriented toward the proximal end of the OTW valvulotome 100. During use, the valvulotome 100 is advanced through the length of a vein in the closed position, then opened and retracted back through the length of the vein to cut the valves.

Figure 5:
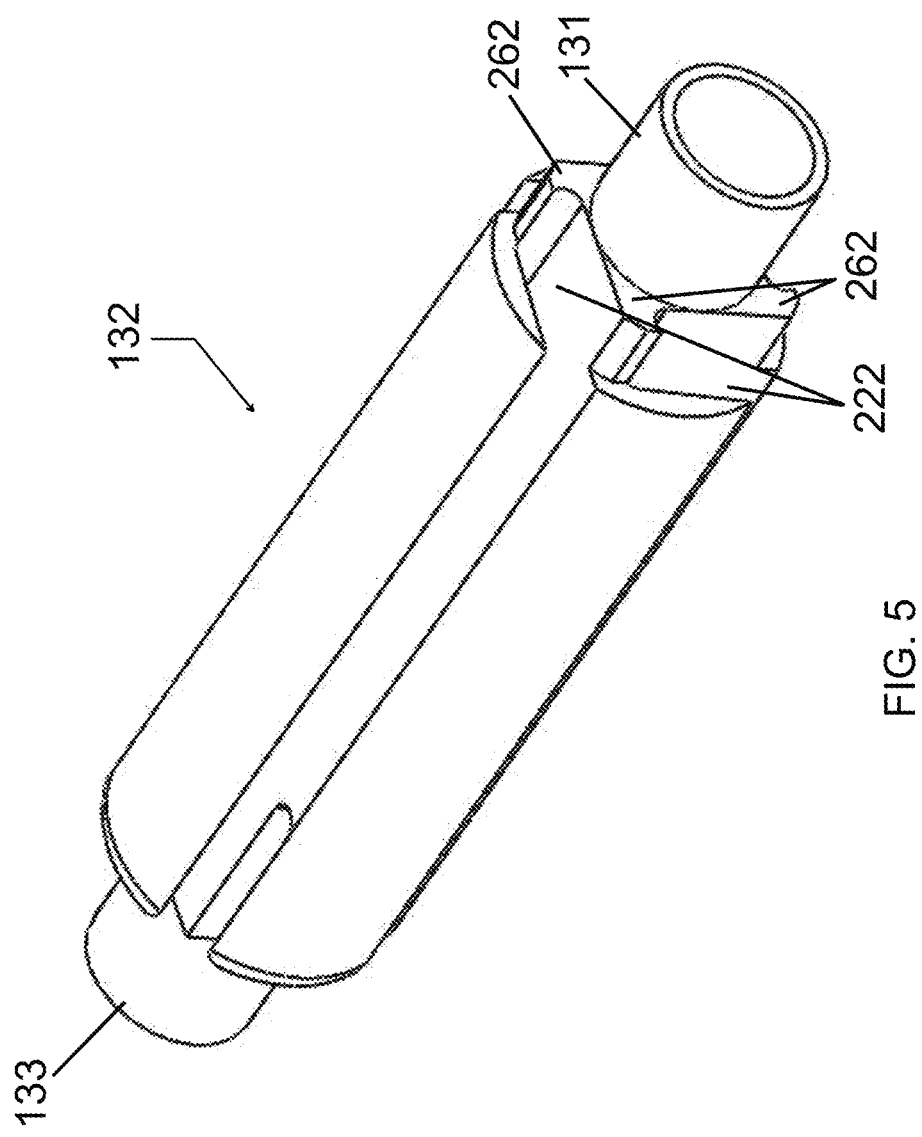
FIG. 5 shows a perspective view of an embodiment of a retainer of the OTW valvulotome of FIG. 1A.

In an embodiment, the self-sizing, self-centering arm 166 helps to keep the OTW valvulotome 100 centered in a vein, allowing for less trauma and more effective valve cutting. The size of the hoops 166 and blades 164 adjust to the internal diameter of a vein as the OTW valvulotome 100 is being drawn through a vessel, thus one size cutting unit 120 allows for effective valve disruption through a wide range of vein diameters. In an embodiment, a thin walled band is suaged or bonded to the catheter 140, for attaching the first end 168 of each of the cutting tools 160 in place. In an embodiment, the thin walled band is manufactured from a metal material. In an embodiment, the thin walled band is manufactured from a plastic material. In an embodiment, the thin walled band is manufactured from a stainless steel material. In an embodiment, catheter 140 is welded or soldered to each end 168. In an embodiment, the catheter 140 may be abraided or laser-ablated to aid the bond. The second end 162 of each cutting tool 160 is free to float up and down within the body of the atraumatic tip 112, and are guided by slots 222 located within the body of the retainer 132, see FIG. 5 in conjunction with FIGS. 6A and 6B. In an embodiment, the slots 222 are axially-oriented slots arranged circumferentially around the retainer 132 at roughly 90° from each other. The OTW valvulotome 100 is sufficiently designed with space constraints in mind, while not sacrificing the self-centering, self-sizing and cutting efficacy behavior of the centering hoops 166/blades 164, the column strength and flexibility of the catheter 140/sheath 170, and the robustness of the device 100.

In an embodiment, the retainer 132 is manufactured from a polymer material. In an embodiment, the retainer 132 is manufactured from a metal material. In an embodiment, the retainer 132 is manufactured from a stainless steel material. In an embodiment, the retainer 132 is manufactured from a molded part. The retainer 132 can be manufactured from any material that provides the necessary strength requirements to be manipulated in situ, and maintain the cutting blades 164 of the cutting tools 160 in position during actuation of the device. The retainer 132 acts as a shelter or garage accommodating the cutting blades 164 of the cutting tools 160. In the abandon or closed position, the cutting blades 164 are encased in the retainer portion 132. The second ends 162 inside atraumatic tip 112 are prevented from exiting the retainer 132 via a hooked head at the distal end of the cutting blades 164, which are prevented from moving past stop positions 262 in the retainer 132.

Figure 6B:
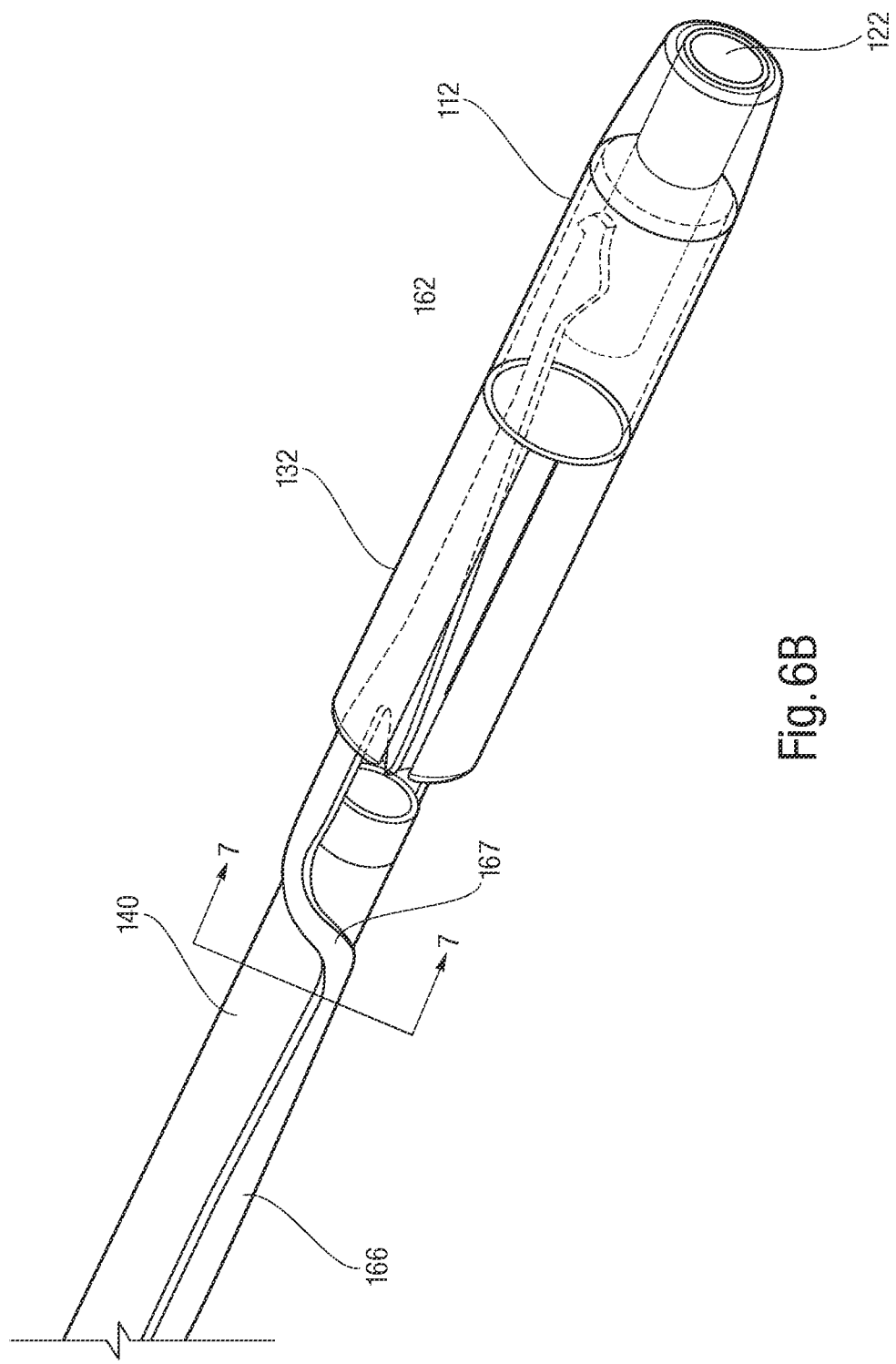
Figure 7:
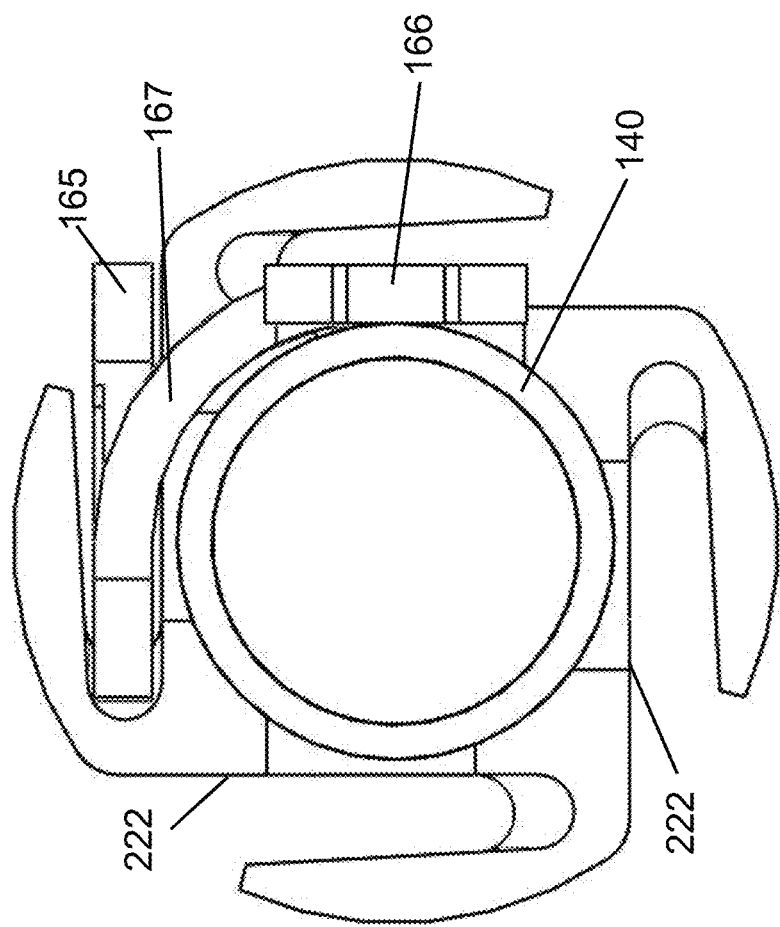
FIG. 7 shows a cutaway view along line 7-7 in FIG. 6B.

In an embodiment, the arm 166 is a flat spring section with resiliency that is sufficiently designed to automatically adjust to different diameter veins. As illustrated in FIGS. 6A and 6B in conjunction with FIG. 7, which shows a cutaway view along line 7-7 of FIG. 6B, a neck 167 of the arm 166 is radially bent/shaped in such a way as to accommodate the catheter 140 underneath and the sheath 170 (not illustrated) overtop. The sheath 170 is slidably positioned over the catheter 140 to retract or sheath the cutting tools 160. In the abandon position, the cutting blades 164 of the cutting unit 120 sit inside the slots 222 of retainer 132. The sheath 170 enables smooth passage of the valvulotome 100 by closing the centering arms 166 of each of the cutting tools 160, thereby parking the cutting blades 164 in a "blade garage".

As illustrated in FIG. 4 in conjunction with FIG. 6A, each cutting tool 160 is constructed so that the self-sizing, self-centering arm 166 extends outward in a radial direction relative to the catheter 140 such that, during use, the distance separating the outermost point of each self-sizing, self-centering arm 166 from the catheter 140 is greater than the distance separating the outermost point of each cutting edge 165 from the catheter 140. When the sheath 170 is slid off the arms 166, the arms 166 open and the blades 164 come out of the retainer 132 (FIG. 6A). The curve of the arm 166 opens farther away from the catheter 140 than the cutting edge 165 of the blade 164. When the valvulotome 100 is used, the arm 166 apposes the vein wall and prevents the edge 165 of the blade 164 from contacting the wall. The edge 165 of the blade 164 is only allowed to contact valves (to cut them). The arms 166 prevent the edge 165 of the blades 164 from cutting the vein wall. As the self-centering arms 166 adjusts to the internal diameter of the vein, the size of the cutting edge 165 is also being adjusted, so as to prevent vein wall trauma. Each cutting blade 164 has an upper, non-cutting outermost edge shielding the cutting edge 165 disposed inwardly therefrom relative to the catheter 140 such that the cutting edge 165 is oriented toward the proximal end of the self-centering valvulotome 100 having a pull handle.

Figure 8:
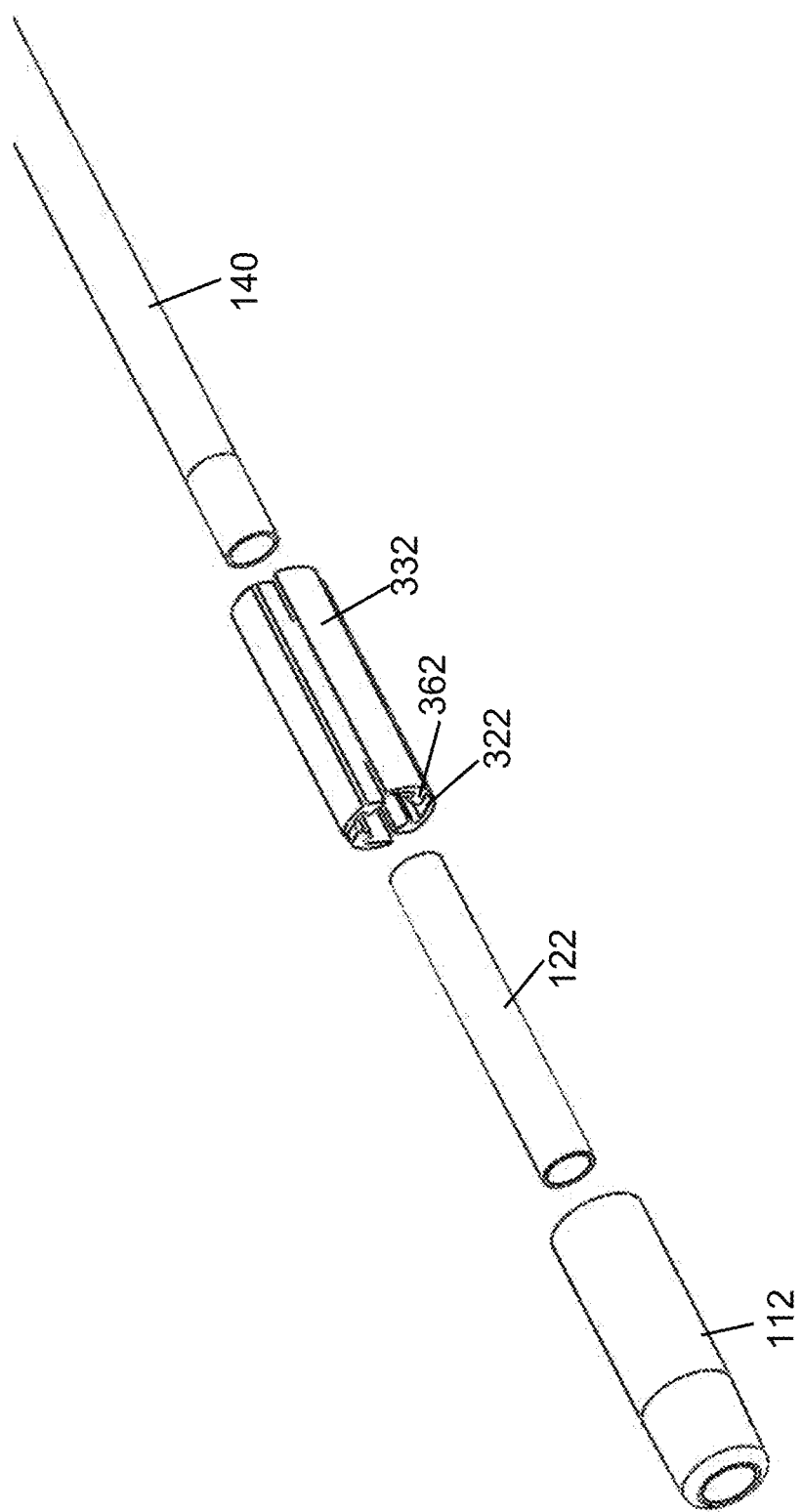
FIG. 8 shows a perspective exploded view of the OTW valvulotome of FIGS. 1A and 2A with an alternative embodiment of a retainer at the distal end thereof.

FIG. 8 shows a perspective exploded view of the OTW valvulotome 100 with an alternative embodiment of a retainer at the distal end thereof. As illustrated in FIG. 8, the distal end of the catheter 140, which, in FIG. 8 is not shown as being laser-cut, is positioned within a proximal end of the body of a retainer 332. The retainer 332 includes slots 322, that serve the same function as slots 222 described above. The second ends 162 are prevented from exiting the retainer 332 via the hooked head at the distal end of the cutting blades 164, which are prevented from moving past stop positions 362 in the retainer 332. A proximal end of the hypotube 122 is positioned within a distal end of the body of the retainer 332, and a distal end of the hypotube 122 can be partially or completely disposed within the atraumatic tip 112. In an embodiment, the catheter 140, the retainer 332, and the hypotube 122 are separate pieces that can be seam-welded, face-welded, butt-welded, spot-welded, soldered, adhesive bonded, chemically bonded or mechanically fastened together. The catheter 140, the retainer 332, and the hypotube 122, when engaged, form a continuous internal channel, allowing the OTW valvulotome 100 to be advanced over a guidewire. In an embodiment, the internal channel amounts to half the cross-sectional area of the distal portion of the OTW valvulotome 100, without a substantial change to the outer diameter. The guidewire would run coaxially through the catheter 140, the retainer 332, the hypotube 122 and the atraumatic tip 112. All other features of the valvulotome 100, including the cutting unit 120 and control mechanism 180 are as described above.

Figure 9:
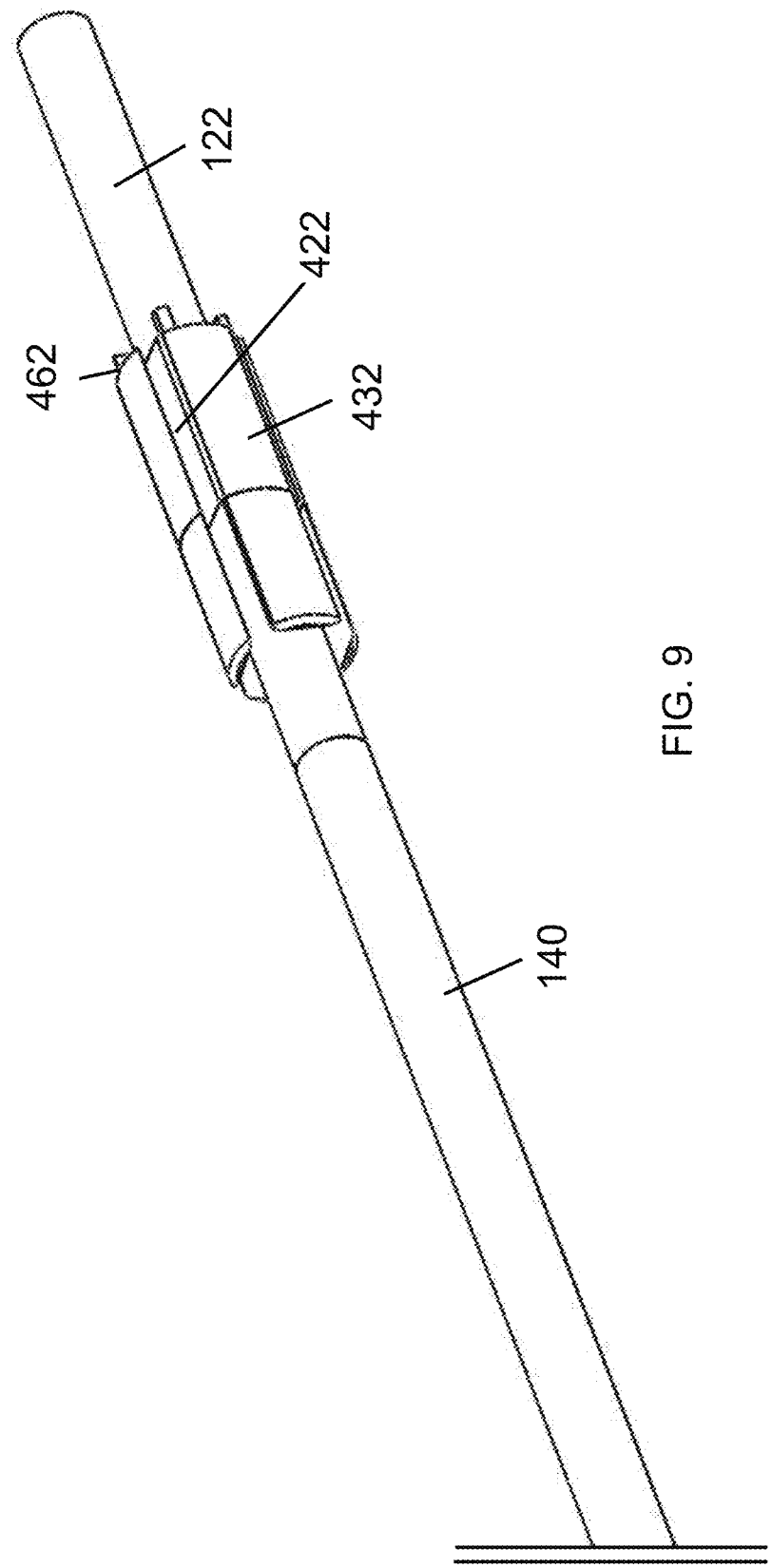
FIG. 9 shows a perspective exploded view of the OTW valvulotome of FIGS. 1A and 2A with an alternative embodiment of a retainer at the distal end thereof.

FIG. 9 shows a perspective exploded view of the OTW valvulotome 100 with an alternative embodiment of a retainer at the distal end thereof. As illustrated in FIG. 9, the distal end of the catheter 140 engages a proximal end of the hypotube 122, wherein a retainer 432 surrounds the hypotube 122. The retainer 432 includes slots 422, that serve the same function as slots 222 and 322 described above. The second ends 162 are prevented from exiting the retainer 432 via the hooked head at the distal end of the cutting blades 164, which are prevented from moving past stop positions 462 in the retainer 432. In an embodiment, the hypotube 122 and the retainer 432 are manufactured as a single unit. In an embodiment, the hypotube 122 and the retainer 432 are manufactured from two separate components. In an embodiment, the retainer 432 is a molded part. In an embodiment, the retainer 432 is insert-molded to a section of the hypotube 122. In an embodiment, the retainer 432 is a separate molded part that is bonded to the hypotube 122. In an embodiment, the hypotube 122 is manufactured from a metal material. In an embodiment, the catheter 140 is bonded to the hypotube 122 just proximal the retainer portion 432. Although not illustrated, in an embodiment, the atraumatic tip 112 is incorporated at the distal end of the hypotube 122. In an embodiment, the catheter 140 and the hypotube 122 are separate pieces that can be seam-welded, face-welded, butt-welded, spot-welded, soldered, adhesive bonded, chemically bonded or mechanically fastened together. The catheter 140 and the hypotube 122, when engaged, form a continuous internal channel, allowing the OTW valvulotome 100 to be advanced over a guidewire. In an embodiment, the internal channel amounts to half the cross-sectional area of the distal portion of the OTW valvulotome 100, without a substantial change to the outer diameter. The guidewire would run coaxially through the catheter 140 and the hypotube 122. All other features of the valvulotome 100, including the cutting unit 120 and control mechanism 180 are as described above.

Figure 10:
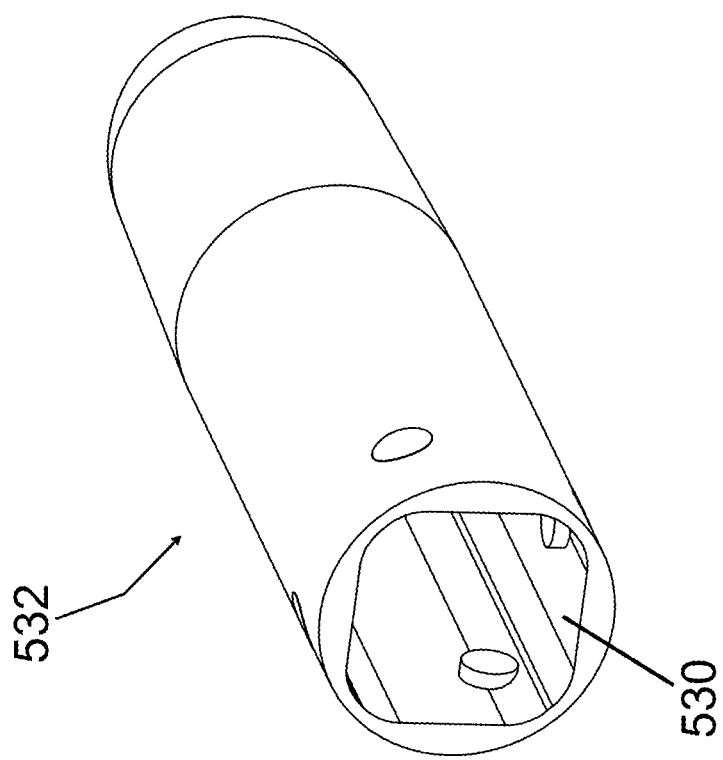
FIG. 10 shows a perspective view of an alternative embodiment of a combination retainer/atraumatic tip for use at the distal end of the OTW valvulotome of FIGS. 1A and 2A.

FIG. 10 shows a perspective view of an alternative embodiment of a combination retainer/atraumatic tip 532 for use at the distal end of the OTW valvulotome of FIGS. 1A and 2A. The retainer/atraumatic tip 532 has an inside square profile 530, thus requiring no slots, in contrast to the slots 222 in retainer 132. The retainer/atraumatic tip 532 is configured to act as both an traumatic tip as well as a garage for the cutting blades 164. In an embodiment, the retainer/atraumatic tip 532 helps to orient the cutting blades 164 correctly. In an embodiment, the cutting blades 164 of the cutting tools 160 would come out the back-end of the retainer/atraumatic tip 532 hybrid (as the sheath 170 is removed) and then open sideways. In an embodiment, slots are designed into the retainer/atraumatic tip 532, thus the cutting blades 164 would come out from the side, as illustrated in FIG. 6B.

In an embodiment, an over-the-wire self-sizing, self-centering expandable valvulotome of the present disclosure includes a catheter having a proximal end, a distal end, and a longitudinal axis therebetween, wherein a first portion of a plurality of cutting tools engage the catheter at the distal end, and wherein an actuation mechanism engages the catheter at the proximal end; a retainer for engaging a second portion of the plurality of cutting tools, wherein the second portion includes cutting blades; and a sheath slidably movable over the plurality of cutting blades, wherein the catheter and the retainer have internal diameters configured for passing over a guidewire. In an embodiment, the actuation mechanism includes a handle portion and an irrigation port. In an embodiment, the handle portion is sufficiently designed to control the positioning of the sheath relative to the plurality of cutting blades. In an embodiment, the retainer is sufficiently designed to function as an atraumatic tip. In an embodiment, the valvulotome further includes an atraumatic tip. In an embodiment, the valvulotome further comprises an atraumatic tip. In an embodiment, the plurality of cutting tools are radially mounted to both the catheter and the retainer. In an embodiment, between the first end and the second end of each cutting tool is a self-sizing, self-centering arm or hoop.

In an embodiment, an over-the-wire self-sizing, self-centering expandable valvulotome of the present disclosure includes a protective sheath having a lumen; a catheter having a catheter lumen, a distal portion, and a proximal portion, the catheter being partly and slidably disposed within the protective sheath; a retainer having a retainer lumen and at least four slots, the retainer fixedly engaging the distal portion of the catheter so as to provide a continuous internal channel for a guidewire; a self-sizing, self-centering cutting unit having at least four cutting tools, wherein each cutting tool comprises: a first end fixedly engaged to the distal portion of the catheter; a second end movably positioned within and guided by the slot of the retainer, the second end having a cutting blade with a recessed cutting edge; a self-sizing, self-centering resilient arm connecting the first end with the second end; and a radially bent shaped neck transitioning between the arm and the second end, the neck sufficiently designed to accommodate an outer circumference of the catheter; and a dual-purpose control mechanism attached to the protective sheath's proximal end and allowing the passage therethrough of the catheter, such that a user of the valvulotome can sheathe and unsheathe the cutting tools by sliding the catheter distally or proximally relative to the protective sheath.

In an embodiment, a method of performing a valvulotomy procedure using an over-the-wire self-sizing, self-centering valvulotome of the present disclosure includes the following procedure: a surgeon places a guidewire in a saphenous vein of a patient to aid in navigation, wherein the guidewire is thought to be an aid when navigating branching vein systems or tortuous saphenous veins; once the proximal end of the saphenous vein has been sutured to the femoral artery, the over-the-wire self-sizing, self-centering valvulotome of the present disclosure, with the cutting blades in a closed sheathed position, is inserted over the guidewire into the distal opening of the vein and advanced to the most proximal segment of the vein; the cutting blades of the valvulotome are opened by slidably moving the sheath relative to the catheter; the valvulotome is withdrawn caudad to excise the valves; the guidewire is left in its original position in the event that a second valvulotome pass is needed; following valvulotomy the distal end of the vein is sutured to the recipient artery and blood is once again able to flow to the foot. Thus the surgeon has "bypassed" the arterial blockage and re-delivered blood to the foot. During use, the construction of the cutting tools is such that the venous valve is opened upon insertion of the valvulotome, but that the vein's natural bloodflow is allowed to close the valve once the cutting tool has passed through, maximizing the destruction of the valve flaps when the cutting tool is withdrawn through the valve.

In an embodiment, a method of performing a valvulotomy procedure includes accessing the vein at both a distal and a proximal point and placing a guidewire in the vein to aid in navigation; inserting an over-the-wire self-sizing, self-centering valvulotome over the guidewire and into the vein at its distal access point, wherein the valvulotome comprises: a catheter having a proximal end, a distal end, and a longitudinal axis therebetween, wherein a first portion of a plurality of cutting tools engage the catheter at the distal end, and wherein an actuation mechanism engages the catheter at the proximal end; a retainer for temporarily shielding a second portion of the plurality of cutting tools, wherein the second portion includes cutting blades; and a sheath slidably movable over the plurality of cutting blades; feeding the valvulotome into the vein with the cutting unit sheathed, until the cutting unit is past a most proximal valve in the vein; manipulating the actuation mechanism to unsheath the cutting unit to release the cutting blades; and withdrawing the valvulotome from the vein, thereby severing each valve in the vein.

In an embodiment, a method of performing a valvulotomy procedure using an over-the-wire self-sizing, self-centering valvulotome of the present disclosure includes selecting a suitable vein for the procedure; accessing the vein at both a distal and a proximal point and segmenting the vein; placing a guidewire in the vein to aid in navigation; inserting an over-the-wire self-sizing, self-centering valvulotome over the guidewire and into the vein segment at its distal access point, wherein the valvulotome comprises: a catheter having a catheter lumen, a distal portion, and a proximal portion; a retainer having a retainer lumen and at least four slots, the retainer fixedly engaging the distal portion of the catheter so as to provide a continuous internal channel for the guidewire; and a self-sizing, self-centering cutting unit having at least four cutting tools, wherein each cutting tool has a first end fixedly engaged to the distal portion of the catheter, a second end movably positioned within and guided by the slot of the retainer, the second end having a cutting blade with a recessed cutting edge, a self-sizing, self-centering resilient arm connecting the first end with the second end, and a radially bent shaped neck transitioning between the arm and the second end, the neck sufficiently designed to accommodate an outer circumference of the catheter; feeding the valvulotome into the vein segment until the cutting unit is past the most proximal valve in the vein segment; and withdrawing the valvulotome from the vein segment, thereby severing each valve in the segment.

All patents, patent applications, and published references cited herein are hereby incorporated by reference in their entirety. It will be appreciated that various of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. An over-the-wire valvulotome comprising:
a catheter having an internal catheter diameter, wherein the internal catheter diameter is sized for passing a guidewire therethrough;
a retainer located at a distal end of the catheter; and
a cutting unit comprising a plurality of self-centering, self-sizing cutting tools, wherein a distal portion of each cutting tool is associated with the retainer, and wherein each cutting tool is designed so when the cutting unit is in a closed position, a portion of each cutting tool is positioned adjacent to an outer circumference of the catheter,
wherein each cutting tool has (i) a first attached end mounted on the distal end of the catheter, (ii) a second free floating end, and (iii) a cutting blade having a recessed cutting edge, and
wherein the retainer includes (i) a plurality of slots in which the second free floating ends of the plurality of cutting tools are guided and (ii) a plurality of stop positions preventing the second free floating ends of the plurality of cutting tools from exiting the retainer.

2. The valvulotome of claim 1 further comprising an actuation mechanism located at the proximal end of the catheter.

3. The valvulotome of claim 2 wherein the actuation mechanism includes a handle portion and an irrigation port.

4. The valvulotome of claim 1 further comprising an atraumatic tip having a body designed to allow the second free floating end of each of the cutting tools to move within the body.

5. The valvulotome of claim 1 further comprising a sheath slidably moveable over the plurality of cutting blades.

6. The valvulotome of claim 5 wherein the sheath is manufactured from polytetrafluoroethylene.

7. An over-the-wire valvulotome comprising:
a sheath having a lumen;
a catheter having an internal catheter diameter, wherein the internal catheter diameter is sized for passing a guidewire through, the catheter being partly and slidably disposed within the sheath;
a retainer located at a distal end of the catheter;
a cutting unit comprising at least two self-centering, self-sizing cutting tools, wherein a distal portion of each cutting tool is associated with the retainer, and wherein each cutting tool is designed so when the cutting unit is in a closed position, a portion of each cutting tool closely surrounds an outer circumference of the catheter; and
an atraumatic tip;
wherein each cutting tool has (i) a first attached end mounted on the distal end of the catheter, (ii) a second free floating end, and (iii) a cutting blade having a recessed cutting edge, and
wherein the retainer includes (i) a plurality of slots in which the second free floating ends of the plurality of cutting tools are guided and (ii) a plurality of stop positions preventing the second free floating ends of the plurality of cutting tools from exiting the retainer.

8. The valvulotome of claim 7 further comprising a dual-purpose control mechanism attached to a proximal end of the sheath and allowing the passage therethrough of the catheter, such that a user of the valvulotome can sheathe and unsheathe the cutting tools by sliding the catheter distally or proximally relative to the sheath.

9. The valvulotome of claim 8 wherein the dual-purpose control mechanism comprises a T-valve segment having a terminal end and an upper end, the T-valve segment being disposed partly within the proximal end of the sheath and the terminal end of the T-valve segment being adapted to allow engagement of a pull handle attached to the proximal end of the catheter.

10. The valvulotome of claim 9 wherein the upper end of the T-valve has an access port.

11. The valvulotome of claim 9 wherein the pull handle engages the terminal end of the T-valve segment to create a fluid-tight seal, thereby allowing the introduction of a diagnostic or therapeutic fluid to the distal end of the sheath via the T-valve access port and the lumen of the protective sheath.

12. The valvulotome of claim 7 wherein the atraumatic tip has a body sufficiently designed to allow the second free floating end of each of the cutting tools to move within the body.

13. The valvulotome of claim 7 wherein the sheath is manufactured from polytetrafluoroethylene.

14. A method of performing a valvulotomy procedure comprising:
inserting a valvulotome over a guidewire and into a vein, wherein the valvulotome comprises:
a catheter having an internal catheter diameter, wherein the internal catheter diameter is sized for passing a guidewire therethrough;
a retainer located at a distal end of the catheter; and
a cutting unit comprising a plurality of self-centering, self-sizing cutting tools with cutting blades, wherein a distal portion of each cutting tool is associated with the retainer, and wherein each cutting tool is designed so when the cutting unit is in a closed position, a portion of each cutting tool is positioned near an outer circumference of the catheter,
wherein each cutting tool has (i) a first attached end mounted on the distal end of the catheter, (ii) a second free floating end, and (iii) a cutting blade having a recessed cutting edge, and
wherein the retainer includes (i) a plurality of slots in which the second free floating ends of the plurality of cutting tools are guided and (ii) a plurality of stop positions preventing the second free floating ends of the plurality of cutting tools from exiting the retainer and (iii) a sheath slidably moveable over the cutting unit;
feeding the valvulotome into the vein with the cutting unit sheathed;
unsheathing the cutting unit to release the cutting blades; and
withdrawing the valvulotome from the vein, thereby severing each valve in the vein.

15. The method of claim 14 further comprising manipulating an actuation mechanism to allow the cutting blades to automatically bias against a vein wall.

* * * * *